US011241440B2

(12) United States Patent
González Fuente et al.

(10) Patent No.: US 11,241,440 B2
(45) Date of Patent: Feb. 8, 2022

(54) DIHYDROOXADIAZINE COMPOUNDS FOR TREATING INFECTIONS AND CANCER

(71) Applicant: VALORALIA I MÁS D, SL, Madrid (ES)

(72) Inventors: Ana María González Fuente, Burgos (ES); Alfredo Hernández Cabanillas, Madrid (ES); Santiago Maderuelo Corral, Madrid (ES); Montserrat Ortega Doménech, Madrid (ES); Diego Fernando Rosero Valencia, Madrid (ES); Ángel Rumbero Sánchez, Madrid (ES); Victor Tena Pérez, Badajoz (ES)

(73) Assignee: Valoralia I Mas D, SL, Madrid (ES)

( * ) Notice: Subject to any disclaimer, the term of this patent is extended or adjusted under 35 U.S.C. 154(b) by 349 days.

(21) Appl. No.: 16/304,797

(22) PCT Filed: Dec. 29, 2016

(86) PCT No.: PCT/EP2016/082843
§ 371 (c)(1),
(2) Date: Nov. 27, 2018

(87) PCT Pub. No.: WO2017/202481
PCT Pub. Date: Nov. 30, 2017

(65) Prior Publication Data
US 2020/0316082 A1  Oct. 8, 2020

(30) Foreign Application Priority Data
May 27, 2016  (EP) .................... 16382237

(51) Int. Cl.
*A61K 31/5395* (2006.01)
*A61P 31/22* (2006.01)
*A61P 31/04* (2006.01)
*A61P 35/04* (2006.01)
*C12P 1/04* (2006.01)

(52) U.S. Cl.
CPC .......... *A61K 31/5395* (2013.01); *A61P 31/04* (2018.01); *A61P 31/22* (2018.01); *A61P 35/04* (2018.01); *C12P 1/04* (2013.01)

(58) Field of Classification Search
CPC .................... A61K 31/5395; C07D 273/04
See application file for complete search history.

(56) References Cited

U.S. PATENT DOCUMENTS

| | | | |
|---|---|---|---|
| 3,537,839 A | 11/1970 | Steinbrunn et al. | |
| 2003/0199541 A1 | 10/2003 | Lampilas et al. | |
| 2005/0020572 A1 | 1/2005 | Aszodi et al. | |
| 2020/0190044 A1* | 6/2020 | Hernández Cabanillas | A61P 31/18 |

FOREIGN PATENT DOCUMENTS

| | | |
|---|---|---|
| CZ | 305944 | 5/2016 |
| GB | 2 091 728 | 12/1980 |
| WO | WO 2003/037349 | 5/2003 |
| WO | WO 2003/062242 | 7/2003 |
| WO | WO 2005/028425 | 3/2005 |
| WO | WO 2014/061825 | 4/2014 |

OTHER PUBLICATIONS

Bosseray et al., PubMed Abstract (Pathol Biol (Paris) 50(8): 483-92), 2002.*
Razonable et al., PubMed Abstract (Herpes 10(3): 60-5), 2003.*
Goff, PubMed Abstract (J Gene Med 3(6): 517-28), 2001.*
Douglas, Jr., Introduction to Viral Diseases, Cecil Textbook of Medicine, 20th Edition, vol. 2, pp. 1739-1747 (1996).*
Simone, Oncology: Introduction, Cecil Textbook of Medicine, 20th Edition, vol. 1, pp. 1004-1010, 1996.*
Acute Leukemia, Merck Manual (Online Edition) 6 pages, pp. 1-6 (2013).*
Pearce et al., Failure modes in anticancer drug discovery and development, Cancer Drug Design and Discovery Edited by Stephen Neidle, Chapter 18, pp. 424-435 (2008).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Berkowitz, P. et al., "Synthesis and Antimicrobial Activity of Certain 6H-1,2,4-Oxadiazin-3(2H)-ones", Journal of Medicinal Chemistry, vol. 20, No. 1, 1977, pp. 134-137.
Bessard, Y. and Crettaz, R., "Rate Acceleration of Nucleophilic Substitution of 2-Chloro-4,6-dimethoxypyrimidine by Sulfinate Catalysis", Tetrahedron, vol. 56, 2000, pp. 4739-4745.
Candelas, N. et al., "More Sustainable Approaches for the Synthesis of N-Based Heterocycles", Chem. Rev., vol. 109, No. 6, 2009, pp. 2703-2802.
Dolle, R. et al., "Comprehensive Survey Of Chemical Libraries for Drug Discovery and Chemical Biology: 2006", Journal of Combinatorial Chemistry, vol. 9, No. 6, 2007, pp. 855-902.
Feliu, L. et al., "Advances in Solid-Phase Cycloadditions for Heterocyclic Synthesis", Journal of Combinatorial Chemistry, vol. 9, No. 4, 2007, pp. 521-565.
Huang, X. et al., "Synthesis and SAR Studies of Fused Oxadiazines as γ-Secretase Modulators for Treatment of Alzheimer's Disease", ACS Medicinal Chemistry Letters, vol. 3, 2012, pp. 931-935.
Ke S. et al., "Novel 4H-1,3,4-Oxadiazin-5(6H)-ones with hydrophobic and long alkyl chains: Design, synthesis, and bioactive diversity on inhibition of monoamine oxidase, chitin biosynthesis and tumor cells", European Journal of Medicinal Chemistry, vol. 44, 2009, pp. 2113-2121.

(Continued)

*Primary Examiner* — Deepak R Rao
(74) *Attorney, Agent, or Firm* — Gary J. Gershik; Amster Rothstein & Ebenstein LLP

(57) ABSTRACT

The invention relates to the use of 1-(4,6-dipentyl-5,6-dihydro-2H-1,2,3-oxadiazin-2-yl)-3-hydroxypropan-1-one in treating and/or preventing infections caused by a bacterium, fungus or virus or in treating and/or preventing cancer. Additionally, the invention relates to a process for obtaining the compound of formula (I) of the invention, said process comprising the steps of cultivating a strain of *Dolichospermum* sp in an aqueous nutrient medium with assimilable carbon and nitrogen sources and salts, under controlled aerobic conditions, and then recovering the compound of general formula (I) from the culture broth.

5 Claims, 7 Drawing Sheets

(56) References Cited

OTHER PUBLICATIONS

Ke S., "Synthesis and Biological Properties of Dihydro-Oxadiazine-Based Heterocyclic Derivatives", Mini-Reviews in Medicinal Chemistry, vol. 11, 2011, pp. 642-657.
López, Ó. et al., "New trends in pest control: the search for greener insecticides", Green Chemistry, vol. 7, 2005, pp. 431-442.
Maqusood, A., "Novel C6-substituted 1,3,4-oxadiazinones as potential anti-cancer agents", Oncotarget, vol. 6, No. 38, 2015, pp. 40598-40610.
Mohareb, R.M. and Schatz, J., "Anti-tumor and anti-leishmanial evaluations of 1,3,4-oxadiazine, pyran derivatives derived from cross-coupling reactions of β-bromo-6H-1,3,4-oxadiazine derivatives", Bioorganic & Medicinal Chemistry, vol. 19, 2011, pp. 2707-2713.
Mousavi, S. et al., "Pyrimidooxadiazine and Triazolopyrimidooxadiazine Derivatives: Synthesis and Cytotoxic Evaluation in Human Cancer Cell Lines", Russian Journal of Bioorganic Chemistry, vol. 41, No. 2, 2015, pp. 201-208.
Naito, T., "Development of New Synthetic Reactions for Nitrogen-Containing Compounds and Their Application", Chem. Pharm. Bull. vol. 56, No. 10, pp. 1367-1383.
Oxborough, R.M., et al., "A new class of insecticide for malaria vector control: evaluation of mosquito nets treated singly with indoxacarb (oxadiazine) or with a pyrethroid mixture against *Anopheles gambiae* and *Culex quinquefasciatus*", Malar J, vol. 14:353, 2015, pp. 1-8.
Garcia-Perez, J. et al., "A New Strategy Based on Recombinant Viruses as a Tool for Assessing Drug Susceptibility of Human Immunodeficiency Virus Type 1", Journal of Medical Virology, vol. 79, 2007, pp. 127-137.
Sicardi, S. M. et al, "New Compounds: 4-Substituted 5,6-Dihydro-2-o-hydroxyphenyl-4H-1,3, 4-oxadiazine-5-ones, Potential Psychopharmacological Drugs", Journal of Pharmaceutical Sciences, vol. 63, No. 8, 1974, pp. 1336-1337.
Stanier, R.Y. et al., "Purification and Properties of Unicellular Blue-Green Algae (Order *Chroococcales*)", Bacteriological Reviews, vol. 35, No. 2, 1971, pp. 171-205.
Tka, N. et al., "Synthesis, antibacterial and antifungal activities of new chiral 5-alkyl-3-(1'-benzenesulfonylpyrrolidin-2'-yl)-4,5-dihydro-1,2,4-oxadiazin-6-ones", Comptes Rendus Chimie, vol. 13, 2010, pp. 1278-1283.
International Search Report issued by the International Searching Authority (ISA/O.E.P.M.) dated Feb. 9, 2017 in connection with International Application No. PCT/EP2016/082843.

\* cited by examiner

DIHYDROOXADIAZINE COMPOUNDS FOR TREATING INFECTIONS AND CANCER

This application is a § 371 national stage of PCT International Application No. PCT/EP2016/082843, filed Dec. 29, 2016, claiming priority of European Patent Application 16382237.2, filed May 27, 2016, the contents of each of which are hereby incorporated by reference into this application.

TECHNICAL FIELD OF INVENTION

The present invention relates to medical treatments for preventing and/or treating infections caused by a bacterium, fungus and/or virus and to treat and/or prevent cancer. The present invention also relates to processes for preparing such compounds.

BACKGROUND OF INVENTION

The discovery of penicillin ushered in the "antibiotic era" and the ability to cure infections which were previously often fatal.

The advantages offered by antibiotics in the treatment of infectious diseases are compromised due to the increase in the number of antibiotic-resistant bacterial strains. Antimicrobial resistance makes it difficult and more expensive to treat a variety of common infections, causing delays in effective treatment, or in worst cases, inability to provide appropriate therapy. The predictable consequences of resistance are increased morbidity, prolonged illness, a greater risk of complications, and higher mortality rates. The economic burden includes loss of productivity (loss in income, diminished worker productivity, time spent by family) and increased cost of diagnostics and treatment (consultation, infrastructure, screening, cost of equipment, drugs . . . ). It has been reported that every year 25000 patients die in the European Union from a bacterial infection which is multi-resistant to the presently existing drugs.

The problem of resistance also covers the major pathogenic fungi and yeasts, encompassing fungal infections, with ever increasing due to their behavior as typical opportunistic. To date, fungal infections continue to be an important cause of morbidity and mortality very high, and may reach up to 100% in some disseminated infections.

Furthermore, cancers have the ability to develop resistance to traditional therapies, and the increasing prevalence of these drug resistant cancers necessitates further research and treatment development. Resistance to treatment with anticancer drugs results from a variety of factors including individual variations in patients and somatic cell genetic differences in tumors, even those from the same tissue of origin.

In addition, although already exists in the market more than 20 anti-HIV drugs, there is a need of new types of antiviral drugs to palliate the new resistances.

The requirements for new antibiotic, antifungal, antitumoral and antiviral molecules are in accordance with current problem of drug and multidrug resistance. It is an increasingly serious threat to global public health that drug resistance is present in all parts of the world. There are now very few effective drugs available to treat recently emerged multidrug resistant infections. Urges the development of new drugs and in this sense, natural products have been a rich source of them for many decades.

Azaheterocyclic compounds display extensive biological activities, which constitute an important class of natural and unnatural products and are extremely versatile building blocks for the manufacture of bioactive compounds in pharmaceutical drug design and agrochemical industry.

Among them, especially those that are six-membered heterocycles being dihydro-oxadiazine skeleton arouse many research interests, which have been demonstrated to be important heterocyclic scaffold platform with bioactive diversity, which present activities such as cardiovascular, antitumor, antibacterial, antimicrobial, acaricidal, insecticidal, plant-growth regulation, chitin biosynthesis inhibitors and monoamine oxidase inhibition (Ke S. et al., Mini Reviews in Medicinal Chemistry, 2011, 642-657).

There is still a need in the state of the art to identify suitable, effective new compounds for the prevention and/or treatment of infections and cancer.

SUMMARY OF THE INVENTION

In a first aspect, the invention relates to the compound 1-(4,6-dipentyl-5,6-dihydro-2H-1,2,3-oxadiazin-2-yl)-3-hydroxypropan-1-one, a pharmaceutically acceptable salt, stereoisomer or solvate thereof, or to a pharmaceutical composition comprising said compound and a pharmaceutically acceptable excipient for use in preventing and/or treating an infection caused by a bacterium, fungus or virus or for use in preventing and/or treating cancer, wherein the cancer is not cervix, liver or pancreatic cancer.

In a second aspect, the invention relates to the process for obtaining a compound of formula (I) or a pharmaceutically acceptable salt, stereoisomer or solvate thereof

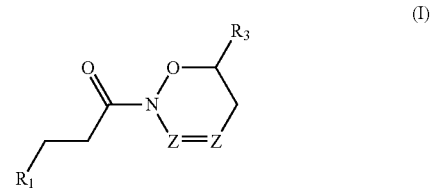

wherein $R_1$ is selected from the group consisting of —H, —$OR_4$, —$SR_4$, —$NR_4R_5$; wherein $R_4$ and $R_5$ are independently selected from the group consisting of —H, —$CH_3$ and —$CH_2CH_3$; one Z is N and the other is —C—$R_2$; and $R_2$ and $R_3$ are independently selected from the group consisting of H, alkyl and aryl, said process comprising the steps of cultivating a strain of *Dolichospermum* sp in an aqueous nutrient medium with assimilable carbon and nitrogen sources and salts, under controlled aerobic conditions, and then recovering the compound of general formula (I) from the culture broth.

DETAILED DESCRIPTION OF THE INVENTION

Figure 1:
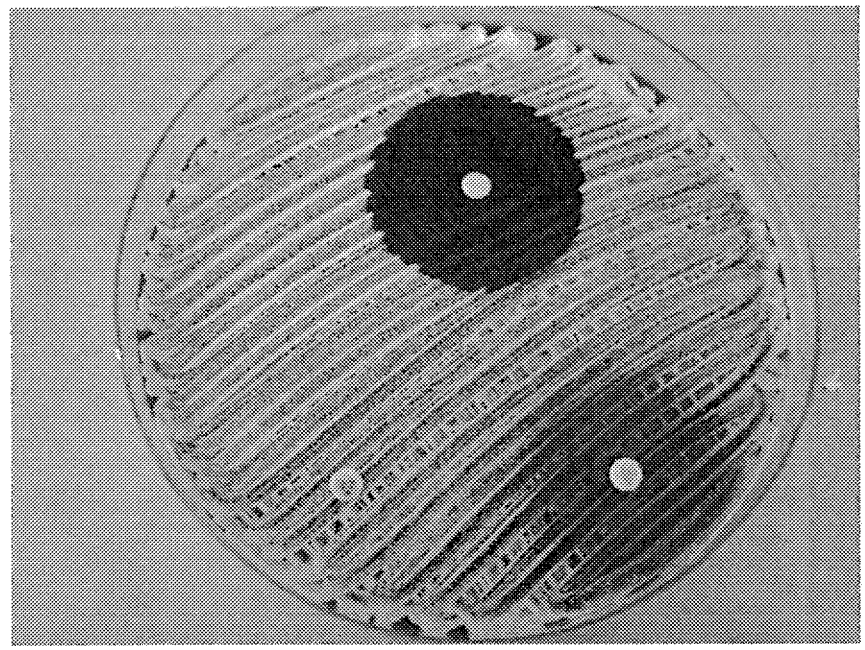
FIG. 1. Activity of the compound in *Nocardia carnea*.

The inventors have identified an oxadiazine compound having antibiotic, antifungal, antiviral and antitumor activity as shown in Examples 2-7.

Medical Uses

In a first aspect, the invention relates to the compound 1-(4,6-dipentyl-5,6-dihydro-2H-1,2,3-oxadiazin-2-yl)-3-hydroxypropan-1-one, a pharmaceutically acceptable salt, stereoisomer or solvate thereof, or to a pharmaceutical composition comprising said compound and a pharmaceutically acceptable excipient for use in preventing and/or treating an infection caused by a bacterium, fungus or virus or for use in preventing and/or treating cancer, wherein the cancer is not cervix, liver or pancreatic cancer.

Alternatively, the invention relates to a method for preventing and/or treating an infection caused by a bacterium, fungus or virus and/or for preventing and/or treating cancer wherein the cancer is not cervix, liver or pancreatic cancer comprising administering the compound 1-(4,6-dipentyl-5, 6-dihydro-2H-1,2,3-oxadiazin-2-yl)-3-hydroxypropan-1-one, a pharmaceutically acceptable salt, stereoisomer or solvate thereof, or a pharmaceutical composition comprising said compound and a pharmaceutically acceptable excipient to a subject in need thereof.

Alternatively, the invention relates to the compound 1-(4, 6-dipentyl-5,6-dihydro-2H-1,2,3-oxadiazin-2-yl)-3-hydroxypropan-1-one, a pharmaceutically acceptable salt, stereoisomer or solvate thereof, or a pharmaceutical composition comprising said compound and a pharmaceutically acceptable excipient for the preparation of a medicament for preventing and/or treating an infection caused by a bacterium, fungus or virus and/or for use in preventing and/or treating cancer wherein the cancer is not cervix, liver or pancreatic cancer.

The medical use of the invention also refers to a pharmaceutically acceptable salt, stereoisomer or solvate of a compound of the invention, 1-(4,6-dipentyl-5,6-dihydro-2H-1,2,3-oxadiazin-2-yl)-3-hydroxypropan-1-one.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition includes in particular physiologically acceptable salts; this term must be understood as equivalent to "pharmacologically acceptable salts" or "pharmaceutically acceptable salts".

The term "physiologically acceptable salt" or "pharmaceutically acceptable salt" is understood in particular, in the context of this invention, as a salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of both. Generally, non-aqueous media like ether, ethyl acetate, ethanol, 2-propanol or acetonitrile are preferred. Examples of the acid addition salts include mineral acid addition salts such as, for example, hydrochloride, hydrobromide, hydroiodide, sulfate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts. Since hydroxytyrosol has three hydroxyl groups, alkali addition salts are particularly preferred such as Na+ and NX4+ (wherein X is independently selected from H or a $C_1$-$C_4$ alkyl group).

For those persons skilled in the art, it will be evident that the scope of the present invention also includes salts which are not pharmaceutically acceptable as possible means for obtaining pharmaceutically acceptable salts.

Any compound referred to herein is intended to represent such specific compound as well as certain variations or forms. The compounds of the present invention include stereoisomers. The term "stereoisomer" as used herein includes any enantiomer, diastereomer or geometric isomer (E/Z) of such compound. In particular, compounds referred to herein may have asymmetric centres and therefore exist in different enantiomeric or diastereomeric forms. Thus any given compound referred to herein is intended to represent any one of a racemate, one or more enantiomeric forms, one or more diastereomeric forms, and mixtures thereof. Likewise, stereoisomerism or geometric isomerism related to a double bond is also possible, therefore in some cases the molecule could exist as (E)-isomer or (Z)-isomer (trans and cis isomers). If the molecule contains several double bonds, each double bond will have its own stereoisomerism, that could be the same or different than the stereoisomerism of the other double bonds of the molecule. All the stereoisomers including enantiomers, diastereoisomers and geometric isomers of the compounds referred to herein, and mixtures thereof, are considered within the scope of the present invention.

The compound of the invention may be in crystalline form either as free compounds or as solvates (e.g. hydrates, alcoholates, particularly methanolates) and it is intended that both forms are within the scope of the present invention. Solvate may include water or non-aqueous solvents such as ethanol, isopropanol, DMSO, acetic acid, ethanolamine, and EtOAc. Solvates, wherein water is the solvent molecule incorporated into the crystal lattice, are typically referred to as "hydrates". Hydrates include stoichiometric hydrates as well as compositions containing variable amounts of water. Methods of solvation are generally known within the art.

When a disclosed compound is named or depicted by structure, it is to be understood that the compound, including solvates thereof, may exist in crystalline forms, non-crystalline forms or a mixture thereof. The compounds or solvates may also exhibit polymorphism (i.e. the capacity to occur in different crystalline forms). These different crystalline forms are typically known as "polymorphs". It is to be understood that when named or depicted by structure, the disclosed compounds and solvates (e.g., hydrates) also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

Furthermore, any compound referred to herein may exist as tautomers. Specifically, the term tautomer refers to one of two or more structural isomers of a compound that exist in equilibrium and are readily converted from one isomeric form to another. Common tautomeric pairs are enamine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compound of the invention or its salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of the invention, or of its pharmaceutically acceptable salt, stereoisomer or solvate.

The invention also provides "metabolites" of the compounds described in the present description. A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups.

The invention also provides "prodrugs" of the compounds described in the present description. The term "prodrug", as used herein, is intended to represent covalently bonded carriers, which are capable of releasing the compound of the invention as active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the invention), amides (e.g., trifluoroacetylamino, acetylamino, and the like), and the like.

The invention also relates to the pharmaceutical composition comprising the compound 1-(4,6-dipentyl-5,6-dihydro-2H-1,2,3-oxadiazin-2-yl)-3-hydroxypropan-1-one, a pharmaceutically acceptable salt, stereoisomer or solvate thereof, and a pharmaceutically acceptable excipient for use in preventing and/or treating an infection caused by a bacterium, fungus or virus or for use in preventing and/or treating cancer, wherein the cancer is not cervix, liver or pancreatic cancer.

"Pharmaceutical composition" as used herein, relates to compositions and molecular entities that are physiologically tolerable and do not typically produce an allergic reaction or a similar unfavorable reaction as gastric disorders, dizziness and suchlike, when administered to a human or animal. Preferably, the term "pharmaceutically acceptable" means it is approved by a regulatory agency of a state or federal government or is included in the U.S. Pharmacopoeia or other generally recognized pharmacopoeia for use in animals, and more particularly in humans.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21$^{st}$ Edition, 2005; or "Handbook of Pharmaceutical Excipients", Rowe C. R.; Paul J. S.; Marian E. Q., sixth Edition.

Appropriate amounts of a compound of the invention, or a pharmaceutically acceptable salt, stereoisomer or solvate thereof can be formulated with pharmaceutically acceptable excipients and/or carriers to obtain a pharmaceutical composition for use in medicine, particularly in preventing and/or treating an infection caused by a bacterium, fungi or virus or preventing and/or treating cancer.

Suitable pharmaceutically acceptable vehicles include, for example, water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and similars.

The pharmaceutical compositions containing the compound of the invention, or a pharmaceutically acceptable salt, stereoisomer or solvate thereof according to the invention can occur at any pharmaceutical form of administration considered appropriate for the selected administration route, for example, by systemic (e.g intravenous, subcutaneous, intramuscular injection), oral, parenteral or topical administration, for which it will include the pharmaceutically acceptable excipients necessary for formulation of the desired method of administration. Additionally, it is also possible to administer the composition comprising the compound of the invention as defined above, or a pharmaceutically acceptable salt, stereoisomer or solvate thereof of the invention intranasally or sublingually which allows systemic administration by a non-aggressive mode of administration. Also, intraventricular administration may be adequate. A preferred route of delivery is oral.

Those skilled in the art are familiar with the principles and procedures discussed in widely known.

Where necessary, the compound of the invention, or a pharmaceutically acceptable salt, stereoisomer or solvate thereof is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration, compounds of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, the compounds of the invention as defined above, or a pharmaceutically acceptable salt, stereoisomer or solvate thereof may be administered in the form of transdermal patches or iontophoresis devices. In one embodiment, the compounds of the invention are administered as a transdermal patch, for example, in the form of sustained-release transdermal patch. Suitable transdermal patches are known in the art.

Several drug delivery systems are known and can be used to administer the agents or compositions of the invention, including, for example, encapsulation in liposomes, microbubbles, emulsions, microparticles, microcapsules and similars. The required dosage can be administered as a single unit or in a sustained release form.

Sustainable-release forms and appropriate materials and methods for their preparation are described in, for example, "Modified-Release Drug Delivery Technology", Rathbone, M. J. Hadgraft, J. and Roberts, M. S. (eds.), Marcel Dekker, Inc., New York (2002), "Handbook of Pharmaceutical Controlled Release Technology", Wise, D. L. (ed.), Marcel Dekker, Inc. New York, (2000). In one embodiment of the invention, the orally administrable form of a compound according to the invention is in a sustained release form further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of the them. Enteric coatings may be applied using conventional processes known to experts in the art, as described in, for example, Johnson, J. L., "Pharmaceutical tablet coating", Coatings Technology Handbook (Second Edition), Satas, D. and Tracton, A. A. (eds), Marcel Dekker, Inc. New York, (2001), Carstensen, T., "Coating Tablets in Advanced Pharmaceutical Solids", Swarbrick, J. (ed.), Marcel Dekker, Inc. New York (2001), 455-468.

The medical uses of the present invention also encompass the combination of the compounds of the invention or of its pharmaceutically acceptable salt, stereoisomer or solvate with other antimicrobial drugs or cancer chemotherapeutic agents. A combination of at least a compound of the invention and at least another antimicrobial drug or cancer chemotherapeutic agents may be formulated for its simultaneous, separate or sequential administration. This has the implication that the combination of the two compounds may be administered:

- as a combination that is being part of the same medicament formulation, the two compounds being then administered always simultaneously.
- as a combination of two units, each with one of the substances giving rise to the possibility of simultaneous, sequential or separate administration.

In a particular embodiment, the compound of the invention is independently administered from the other antimicrobial drug or cancer chemotherapeutic agent (i.e in two units) but at the same time.

In another particular embodiment, the compound of the invention is administered first, and then the other antimicrobial drug or cancer chemotherapeutic agent is separately or sequentially administered.

In yet another particular embodiment, the other antimicrobial drug or cancer chemotherapeutic agent is administered first, and then the compound of the invention is administered, separately or sequentially, as defined.

"Antimicrobial drug", as used herein, relates to any drug capable of killing bacteria, viruses, fungi or parasites or inhibit their growth. Antimicrobial medicines can be grouped according to the microorganisms they act primarily against, antibacterial, antifungal, antiviral and antiparasitic.

The term "cancer chemotherapeutic agent" includes standard chemotherapy drugs, which generally attack any quickly dividing cell, targeted therapy agents and immunomodulatory agents.

Illustrative non-limitative examples of cancer chemotherapeutic agents which may be in accordance to the present invention include alkylating agents, antimetabolite drugs, anthracycline antibiotics, antibodies targeted against proangiogenic factors, topoisomerase inhibitors, antimicrotubule agents, low molecular weight tyrosine kinases inhibitors of proangiogenic growth factors and matrix metalloproteinase inhibitors.

The medical use of the invention relates to the prevention and/or treatment of an infection caused by a bacterium, fungus or virus or to the prevention and/or treatment of cancer, wherein the cancer is not cervix, liver or pancreatic cancer.

As used herein, the terms "treat", "treating" and "treatment" include in general the eradication, removal, reversion, alleviation, modification, or control of the infection or cancer after its onset.

As used herein, the terms "prevention", "preventing", "preventive", "prevent" and "prophylaxis" refer to the capacity of a given substance, composition or medicament to avoid, minimize or difficult the onset or development of an infection or cancer before its onset.

The term "subject" as used herein, relates to any subject, particularly a mammalian subject, for whom therapy is desired. Mammalian subjects include humans, domestic animals, farm animals, and zoo, sports, or pet animals such as dogs, cats, guinea pigs, rabbits, rats, mice, horses, cattle, cows, and so on. In a preferred embodiment of the invention, the subject is a mammal. In a more preferred embodiment of the invention, the subject is a human.

The term "infection", as used herein, relates to invasion by bacteria, viruses, fungi, protozoa or other microorganisms, referring to the undesired proliferation or presence of invasion of pathogenic microbes in a host organism. It includes the excessive growth of microbes that are normally present in or on the body of a mammal or other organism. More generally, a microbial infection can be any situation in which the presence of a microbial population(s) is damaging to a host mammal. Thus, a microbial infection exists when excessive numbers of a microbial population are present in or on a mammal's body, or when the effects of the presence of a microbial population(s) is damaging the cells or other tissue of a mammal.

In a preferred embodiment, the infection is caused by a bacterium.

The term "bacterium" refers to both gram-negative and gram-positive bacterial cells capable of infecting and causing disease in a mammalian host, as well as producing infection-related symptoms in the infected host, such as fever or other signs of inflammation, intestinal symptoms, respiratory symptoms, dehydration, and the like.

In one embodiment the bacteria are gram-negative bacteria. In another embodiment the bacteria are gram-positive bacteria. In another further embodiment the bacteria are gram-positive bacteria together with gram-negative bacteria. In another embodiment there is only one bacteria specie or different bacteria species; one bacteria genus or different bacteria genus, infecting or causing disease.

In some embodiments, and without limitation, the bacteria is of a genus selected from the group consisting of *Acinetobacter, Actinobacillus, Aeromonas, Aggregatibacter, Agrobacterium, Bacillus, Bordetella, Brucella, Burkholderia, Campylobacter, Chromobacterium, Cyanobacteria, Enterobacter, Erwinia, Escherichia, Francisella, Fusobacterium, Haemophilus, Helicobacter, Klebsiella, Lactobacillus, Legionella, Listeria, Micrococcus, Moraxella, Mycobacterium, Neisseria, Nitrosomas, Nocardia, Obesumbacterium, Pantoea, Pasteurella, Pediococcus, Porphyromonas, Prevotella, Proteus, Pseudomonas, Ralstonia, Rhizobium, Rhodobacter, Salmonella, Serratia, Shigella, Staphylococcus, Streptococcus, Tannerella, Treponema, Tsukamurella, Vibrio, Xenorhabdus, Yersinia* and mixtures thereof. For example, in some embodiments and without limitation, the bacteria is of a species selected from the group consisting of *Aeromonas hydrophila, Aeromonas salmonicida, Acinetobacter baumannii, Aggregatibacter actinomycetemcomitans, Agrobacterium tumefaciens, Bacillus cereus, Bacillus subtilis, Burkholderia cepacia, Campylobacter jejuni, Chromobacterium violaceum, Enterobacter agglomeran, Erwinia carotovora, Erwinia chrysanthemi, Escherichia coli, Fusobacterium nucleatum, Haemophilus influenzae, Helicobacter pylori, Lactobacillus plantarum, Listeria monocytogenes, Klebsiella pneumoniae, Micrococcus luteus, Mycobacterium tuberculosis, Neisseria meningitidis, Neisseria gonorrhoeae, Nitrosomas europaea, Nocardia carnea, Obesumbacterium proteus, Pantoea stewartii, Pediococcus acidilactici, Prevotella intermedia, Porphyromonas gingivalis, Pseudomonas aureofaciens, Pseudomonas aeruginosa, Pseudomonas phosphoreum, Pseudomonas syringae, Ralstonia solanacearum, Rhiszobium etli, Rhizobium leguminosarum, Rhodobacter sphaeroides, Salmonella typhimurium, Serratia liguefaciens, Serratia marcescens, Staphylococcus aureus, Staphylococcus epidermidis, Staphylococcus enteritis, Tannerella forsythensis, Treponema denticola, Tsukamurella pulmonis, Vibrio anguillarum, Vibrio fischeri, Vibrio cholerae, harveyi, Vibrio parahaemolyticus, Vibrio alginolyticus, Vibrio vulnificus, Xenorhabdus nematophilus, Yersinia enterocolitica, Yersinia pestis, Yersinia pseudotuberculosis, Yersinia medievalis, Yersinia ruckeri* and mixtures thereof.

In a preferred embodiment of the medical use of a compound, or a pharmaceutically acceptable salt, stereoisomer or solvate thereof or pharmaceutical composition of the invention as defined above, the infection is caused by a Gram positive bacterium.

In another preferred embodiment, the Gram positive bacterium is from phylum Actinobacteria or from phylum Firmicutes.

In a more preferred embodiment, the bacterium from phylum Actinobacteria is a bacterium from genus *Nocardia, Tsukamurella* or *Mycobacterium* and the bacterium from phylum Firmicutes is a bacterium from genus *Staphylococcus* or *Bacillus*. In a more preferred embodiment, the bacterium from the genus *Nocardia* is N cornea or *N. cyriacigeorgica*, the bacterium from genus *Tsukamurella* is *T. pulmonis*, the bacterium from genus *Mycobacterium* is M chelonae, M *abscessus* or *M. fortuitum*, the bacterium from genus *Staphylococcus* is *S. aureus* or *S. epidermidis* and the bacterium from genus *Bacillus* is *B. cereus*.

In another preferred embodiment, the Gram negative bacterium is from phylum proteobacteria. In a more preferred embodiment, bacterium from phylum proteobacteria is from genus *Acinetobacter*, preferably *A. baumannii*.

In another preferred embodiment of the medical use of a compound of the invention as defined above, or a pharmaceutically acceptable salt, stereoisomer or solvate thereof, the infection is caused by a fungus. In a more preferred embodiment, the fungus is selected from genus *Candida*, *Aspergillus* or *Scedosporium*. In an even more preferably embodiment, the fungus from genus *Candida* is *C. parapsilopsis*, the fungus from genus *Aspergillus* is *A. fumigatus*, *A. flavus* or *A. terreus* and the fungus from genus *Scedasporium* is *S. prolificans*.

In another preferred embodiment of the medical use of a compound of the invention as defined above, or a pharmaceutically acceptable salt, stereoisomer or solvate thereof, the infection is caused by a virus.

The term "virus", refers to a small infectious agent that replicates only inside the living cells of other organism.

In some embodiments, and without limitation, the virus is selected from the group consisting of adenovirus, coxsackievirus, Epstein-Bar, Hepatitis A, B or C, herpes simplex type 1, herpes simplex type 2, cytomegalovirus, herpesvirus type 8, HIV, Influenza, Measles, mumps, human papillomavirus, parainfluenza, poliovirus, rabies, respiratory syncytial, rubella, varicella-zoster. In a preferred embodiment the virus is selected from HIV, herpes simplex I, herpes simplex II, Suid herpesvirus 1, pseudorabies virus, particularly porcine pseudorabies virus, or Equine herpesvirus 1.

In another preferred embodiment, the compound or the pharmaceutical composition of the invention is for use in the prevention and/or treatment of cancer, wherein the cancer is not cervix, liver or pancreatic cancer.

The term "cancer" as used herein, refers to a disease characterized by uncontrolled cell division (or by an increase of survival or apoptosis resistance) and by the ability of said cells to invade other neighbouring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. As used herein, the term cancer includes, but is not limited to, the following types of cancer: breast cancer; biliary tract cancer; bladder cancer; brain cancer including glioblastomas, in particular glioblastoma multiforme, and medulloblastomas; cervical cancer; head and neck carcinoma; choriocarcinoma; colon cancer, colorectal cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; lung cancer, pleural mesothelioma; lymphomas including Hodgkin's disease and lymphocytic lymphomas; neuroblastomas; oral cancer including squamous cell carcinoma; parotid gland cancer; ovarian cancer including those arising from epithelial cells, stromal cells, germ cells and mesenchymal cells; prostate cancer; kidney cancer, suprarenal cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; endometrial cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill.

In a preferred embodiment, the cancer is selected from the group consisting of breast, head and neck, colon, prostate, lung, glioblastoma and osteosarcoma.

The present invention covers any combination of compounds and diseases.

For use in the prevention and/or treatment according to the invention, the compound of the invention or a pharmaceutically acceptable salt, solvate or isomer thereof or the pharmaceutical composition of the invention is present in an effective amount.

The term "effective" amount or a "therapeutically effective amount" of a drug or pharmacologically active agent is meant a nontoxic but sufficient amount of the drug or agent to provide the desired effect. In the combination therapy of the present invention, an "effective amount" of one component of the combination is the amount of that compound that is effective to provide the desired effect when used in combination with the other components of the combination.

Even though individual needs vary, determination of optimal ranges for effective amounts of the agent of the invention belongs to the common experience of those experts in the art. In general, the dosage needed to provide an effective amount of such compound, which can be adjusted by one expert in the art will vary depending on age, health, fitness, sex, diet, weight, frequency of treatment and the nature and extent of impairment or illness, medical condition of the patient, route of administration, pharmacological considerations such as activity, efficacy, pharmacokinetic and toxicology profile of the particular compound used, if using a system drug delivery, and if the compound is administered as part of a combination of drugs.

The effective quantity of the compound of the invention can vary within a wide range and, in general, will vary depending on the particular circumstances of application, duration of the exposure and other considerations. In a particular embodiment, the dose ranges between 0.05 mg/kg and 50 mg/kg, more preferably between 1 mg/kg and 20 mg/kg.

In a preferred embodiment the effective amount is between about 0.005% and about 0.04% weight, between about 0.0075% weight and about 0.0375% weight, between about 0.001% weight and about 0.035% weight, between about 0.00125% weight and about 0.0325% weight, between about 0.0015% weight and about 0.0325% weight, between about 0.00175% weight and about 0.03% weight, and more preferably between about 0.0018% weight and about 0.032% weight. In a particular embodiment, the effective amount is between about 0.005% and about 0.02% weight, preferably between about 0.005% weight and about 0.015% weight, more preferably between about 0.005% weight and about 0.01% weight. In some embodiments the effective amount is about 0.001% weight, about 0.002% weight, about 0.003% weight or about 0.004% weight. The percentages (% w/w) are expressed as weight of the compound of the invention or a pharmaceutically acceptable salt, solvate or isomer thereof by the total weight of the composition comprising the compound or by weight of the foodstuff, foodstuff package, medical device or surface.

In another embodiment the effective amount is expressed in μg/mL or μg/g (μg of the compound of the invention or a pharmaceutically acceptable salt, solvate or isomer thereof by mL or g of the composition comprising the compound, therefore effective amount is about 75 and about 375 μg/mL (or μg/g), between about 100 and about 350 μg/mL (or μg/g), between about 125 and about 325 μg/mL (or μg/g), between about 150 and about 325 μg/mL (or μg/g), between about 175 and about 300 μg/mL (or μg/g), and more preferably between about 180 and about 320 μg/mL (or μg/g). In a particular embodiment, the effective amount is between about 50 and about 200 μg/mL (or μg/g), preferably between 50 and about 150 μg/mL (or μg/g), more preferably between about 50 and about 100 μg/mL (or μg/g). In some embodiments the effective amount is about 100 μg/mL (or μg/g), about 200 μg/mL (or μg/g), about 300 μg/mL (or μg/g) or about 400 μg/mL (or μg/g).

When the compound of the invention or a salt, solvate or isomer thereof as defined herein is present on a surface, it is preferably in an effective amount of between about 1 and about 200 μg/cm$^2$, preferably between about 1 and about 1.00 μg/cm$^2$, preferably between about 1 and about 50 μg/cm$^2$, more preferably between about 5 and about 300 μg/cm$^2$.

Process for Obtaining New Compounds

In another aspect, the invention relates to a process for obtaining a compound of formula (I) or a pharmaceutically acceptable salt, stereoisomer or solvate thereof

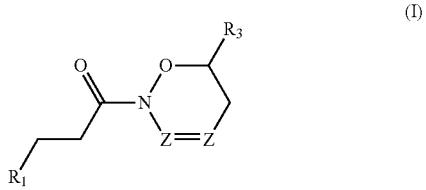

(I)

wherein
$R_1$ is selected from the group consisting of —H, —OR$_4$, —SR$_4$, —NR$_4$R$_5$; wherein $R_4$ and $R_5$ are independently selected from the group consisting of —H, —CH$_3$ and —CH$_2$CH$_3$; one Z is N and the other is —C—R$_2$; and $R_2$ and $R_3$ are independently selected from the group consisting of H, alkyl and aryl, said process comprising the steps of cultivating a strain of *Dolichospermum* sp. in an aqueous nutrient medium with assimilable carbon and nitrogen sources and salts, under controlled aerobic conditions, and then recovering the compound of general formula (I) from the culture broth.

"Alkyl" refers to a straight or branched hydrocarbon chain radical consisting of carbon and hydrogen atoms, containing no unsaturation, and which is attached to the rest of the molecule by a single bond. Alkyl groups having 1, 2, 3, 4, 5, 6, or 7 carbon atoms are particularly preferred. Methyl, ethyl, n-propyl, iso-propyl and butyl, pentyl, hexyl, heptyl, including n-butyl, tert-butyl, sec-butyl and iso-butyl are particularly preferred alkyl groups. As used herein, the term alkyl, unless otherwise stated, refers to both cyclic and noncyclic groups, although cyclic groups will comprise at least three carbon ring members, such as cyclopropyl or cyclohexyl. Alkyl radicals may be optionally substituted by one or more substituents, such as an aryl group, like in benzyl or phenethyl. In a more preferred embodiment, the alkyl is C$_1$-C$_6$ alkyl. In a more preferred embodiment, the C$_1$-C$_6$ alkyl is selected from the group consisting of —CH$_3$, —CH$_2$CH$_3$, —(CH$_2$)$_2$CH$_3$, —(CH$_2$)$_3$CH$_3$, —(CH$_2$)$_4$CH$_3$ and —(CH$_2$)$_5$CH$_3$.

"Aryl" as used herein relates to single and multiple ring compounds, including multiple ring compounds that contain separate and/or fused aryl groups. Typical aryl groups contain from 1 to 3 separated and/or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl. The term includes but is not limited to, phenyl, naphthyl, tetrahydronaphthyl, indanyl, indenyl, and the like. In a preferred embodiment the aryl is phenyl.

In a preferred embodiment —OR$_4$ is —OH or —OCH$_3$. In another preferred embodiment —SR$_4$. is —SH or —SCH$_3$. In another preferred embodiment —NR$_4$R$_5$ is —NH$_2$ or —N(CH$_2$CH$_3$)$_2$.

In another preferred embodiment, the compound according to the invention is the compound of formula

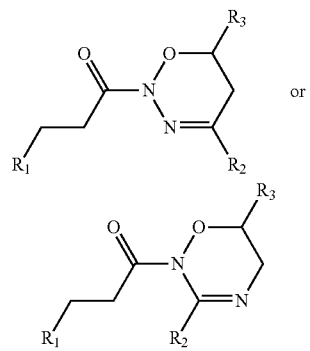

In another preferred embodiment, $R_2$ and $R_3$ are the same group. In a more preferred embodiment, the compound of the invention is the compound of formula

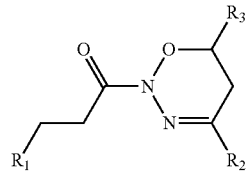

In a more preferred embodiment, the compound is

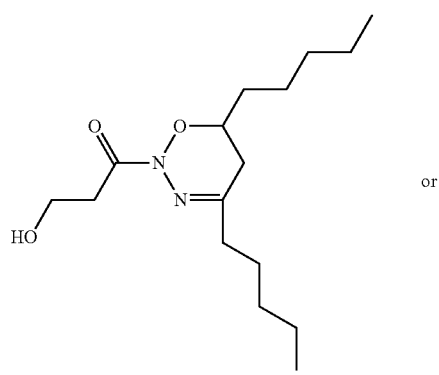

-continued

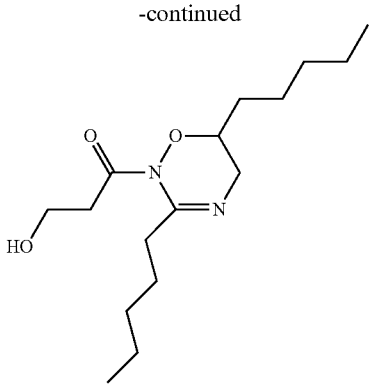

In a more preferred embodiment, the compound is

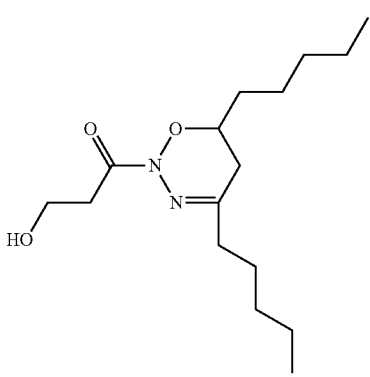

alternatively 1-(4,6-dipentyl-5,6-dihydro-2H-1,2,3-oxadiazin-2-yl)-3-hydroxypropan-1-one.

In additional preferred embodiments, the preferences described above for the different groups and substituents in the formulae above are combined. The present invention is also directed to such combinations.

The compounds of the invention may be produced by cultivating a strain of *Dolichospermum* sp. in a suitable nutrient medium, such as those described below, until a significant amount accumulates in the fermentation.

In a preferred embodiment the strain of *Dolichospermum* sp. is the strain BEA0942B from Banco Espanol de Algas, which is freely available from said depositary institution.

The strain is usually cultured in an aqueous nutrient medium containing sources of assimilable carbon and nitrogen. In a preferred embodiment, the culture is grown in the presence of light. The cultures may be grown under submerged aerobic conditions (e.g., shaking the culture, submerging the culture, etc.) or in solid state fermentations. The aqueous medium is preferably maintained at a pH of about 6-8, at the initiation and termination (harvest) of the fermentation process. The desired pH may be maintained by the use of a buffer, such as morpholinoethane-sulfonic acid (MES), morpholinopropane-sulfonic acid (MOPS), and the like, or by choosing nutrient materials that inherently possess buffering properties. The skilled person in the art knows several aqueous nutrient medium containing sources of assimilable carbon and nitrogen suitable for use in the present invention. Suitable sources of carbon in the nutrient medium include carbohydrates, such as glucose, xylose, galactose, glycerine, starch, sucrose, dextrin and the like. Other suitable carbon sources that may be used include maltose, rhamnose, raffinose, arabinose, mannose, sodium succinate and the like. Suitable sources of nitrogen are yeast extracts, meat extracts, peptone, gluten meal, cottonseed meal, soybean meal and other vegetable meals (partially or totally defatted), casein hydrolysates, soybean hydrolysates, yeast hydrolysates, corn steep liquor, dried yeast, wheat germ, feather meal, peanut powder, distiller's solubles and the like, as well as inorganic and organic nitrogen compounds, such as ammonium salts (including ammonium nitrate, ammonium sulfate, ammonium phosphate, etc.), urea, amino acids, and the like. The carbon and nitrogen sources, which may be advantageously employed in combination, do not need be used in their pure forms; because less pure materials, which contain traces of growth factors, vitamins and significant quantities of mineral nutrients, are also suitable for use. In the case it would be necessary, mineral salts, such as sodium or calcium carbonate, sodium or potassium phosphate, sodium or potassium chloride, sodium or potassium iodide, magnesium salts, copper salts, cobalt salts, and the like, may be added to the medium. If necessary, especially when a culture medium foams excessively, one or more defoaming agent(s), such as liquid paraffin, fatty oils, plant oils, mineral oils or silicones, may be added. Submerged aerobic cultural conditions are typical methods of culturing cells for the production of cells in massive amounts. For small-scale production, a shaken or surface culture in a flask or bottle may be employed. When growth is carried out in large tanks, it may be preferable to use the vegetative forms of the organism for inoculation in the production tanks in order to avoid growth lag in the process of production. Accordingly, it may be desirable first to produce a vegetative inoculum of the organism by inoculating a relatively small quantity of culture medium with spores or mycelia of the organism produced in a "slant" or Petri dish and culturing said inoculated medium, also called the "seed medium," and then to transfer the cultured vegetative inoculum aseptically to large tanks. The fermentation medium, in which the inoculum is produced, is generally autoclaved to sterilize the medium prior to inoculation. The pH of the medium is generally adjusted to about 6-7 prior to the autoclaving step. Agitation and aeration of the culture mixture may be accomplished in a variety of ways. Agitation may be provided by a propeller or similar mechanical agitation equipment, by revolving or shaking the fermentor, by various pumping equipment, or by the passage of sterile air through the medium. The fermentation is usually conducted at a temperature between about 20° C. and 30° C., such as between about 22° C. and 25° C., for a period of about 7 to 21 days, and parameters may be varied according to fermentation conditions and scales. Preferred culturing/production media for carrying out the fermentation include the media as set forth in the examples. Culture media such as BG11 (Stanier R. Y., et al., 1971, Bacteriol. Rev., 35: 171-205) is particularly preferred.

In a preferred embodiment, the process of obtaining a compound of formula (I) as defined above, or a pharmaceutically acceptable salt, stereoisomer or solvate thereof further comprises purifying the compound recovered from the culture broth.

Separation and purification of the compounds of the present invention from the crude active extract can be performed using any method known in the art such as the proper combination of conventional chromatographic techniques.

Additionally, compounds of the invention can be obtained by modifying those already obtained from the natural source or by further modifying those already modified by using a variety of chemical reactions, for instance by means of derivatization, protection/deprotection and isomerisation reactions. Thus, hydroxyl groups can be acylated by standard coupling or acylation procedures, for instance by using acetic acid, acetyl chloride or acetic anhydride in pyridine or the like. Formate groups can be obtained by heating hydroxyl precursors in formic acid. Carbamates can be obtained by heating hydroxyl precursors with isocyanates. Hydroxyl groups can be converted into halogen groups through intermediate sulfonates for iodide, bromide or chloride, or directly using a sulfur trifluoride for fluorides; or they can be reduced to hydrogen by reduction of intermediate sulfonates. Hydroxyl groups can also be converted into alkoxy groups by alkylation using an alkyl bromide, iodide or sulfonate, or into amino lower alkoxy groups by using, for instance, a protected 2-bromoethylamine. Amide groups can be alkylated or acylated by standard alkylation or acylation procedures, for instance by using, respectively, KH and methyl iodide or acetyl chloride in pyridine or the like. Ester groups can be hydrolized to carboxylic acids or reduced to aldehyde or to alcohol. Carboxylic acids can be coupled with amines to provide amides by standard coupling or acylation procedures. Carbonyl compounds can be reduced to alcohols by standard procedures. Double bonds can be epoxidized by known methods. When necessary, appropriate protecting groups can be used on the substituents to ensure that reactive groups are not affected. The procedures and reagents needed to prepare these derivatives are known to the skilled person and can be found in general textbooks such as March's Advanced Organic Chemistry 6th Edition 2007, Wiley Interscience. As the skilled person will appreciate, certain compounds of formula (I) may be useful as intermediate products in the preparation of other compounds of formula (I).

All the terms and embodiments previously described are equally applicable to this aspect of the invention.

The invention will be described by way of the following examples which are to be considered as merely illustrative and not limitative of the scope of the invention.

Materials and Methods

Production of the Compound

The oxadiazine was identified from a strain of cyanobacteria, specifically *Dolichospermum* sp. strain BEA0942B from Banco Español de Algas. The biomass (cellular mass) was obtained from a culture grown in the BG11 medium under described and standardized conditions (Stanier, R. Y. et al., Bacteriol. Rev. June 1971 35(2):171-205).

The freeze-dried biomass (8.9 g) was extracted by repeated maceration with $CH_2Cl_2$/MeOH (1:1) to yield 1.84 g of crude extract. The crude showed high biological activities. Organic extract was subjected to silica gel column chromatography (CC) antimicrobial-bioguied, using a stepwise gradient of $CH_2Cl_2$:MeOH to produce 3 fractions (A-C). Fraction B, eluting with 30 $CH_2Cl_2$ in 1 MeOH was found to be the most active. This fraction was subjected to bioactivity-guided fractionation using silica gel chromatography column, eluting with 1 Hexane in 1 Ethyl acetate to afford the compound (8 mg, 0.08%).

Chemical Characterization of the Compound

The compound used in the examples is 1-(4,6-dipentyl-5,6-dihydro-2H-1,2,3-oxadiazin-2-yl)-3-hydroxypropan-1-one and was found to have the following structure:

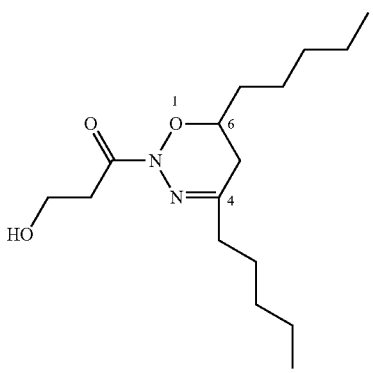 [SMILES: CCCCCC1=NN(C(=O)CCO)OC(CCCCC)C1]

The new compound structure was assigned by interpretation of their spectral characteristics 1H-NMR, 13C-NMR, DEPT, HH-COSY, H-C HSQC, HSQC-TOCSY, H-C HMBC, H-N-HMBC and mass spectral features. The spectral features was recorded as follows: $[M+Na]^+$ calculated m/z 321.2149, found m/z 321.2152 $[M+H]^+$ m/z 299.2346. A molecular formula of $C_{16}H_{30}N_2O_3$ was obtained from MS and from 13C-NMR (DEPT) analysis. Examination of NMR data suggested that the new compound was a 1,2,3-oxadiazine ring with two alkyl chains at C-4 and C-6, and 3-hydroxipropan-2-one chain at N-2. (500 MHz, $CDCl_3$): δ 0.89 (t, J=6.8 Hz, 3H), 0.90 (t, J=6.8 Hz, 3H), 1.30-1.35 (m, 8H), 1.42 (m, 1H), 1.50 (m, 1H), 1.53 (m, 1H), 1.56 (m, 2H), 1.72 (m, 1H), 2.16 (dd, J=18.1, 8.9 Hz, 1H), 2.25 (t, J=6.9 Hz, 2H), 2.27 (dd, J=18.1, 3.9 Hz, 1H), 2.83 (dt, J=17.2, 5.2 Hz, 1H), 2.88 (dt, J=17.2, 5.2 Hz, 1H), 3.91 (t, J=5.2 Hz, 2($CH_2$), H), 4.05 (m, 1H). $^{13}$C-NMR (125 MHz, $CDCl_3$): δ 13.99 (2 $CH_3$), 22.43 ($CH_2$), 22.45 ($CH_2$), 24.36 ($CH_2$), 25.62 ($CH_2$), 31.34 ($CH_2$), 31.62 ($CH_2$), 31.70 ($CH_2$), 33.95 ($CH_2$), 35.79 ($CH_2$), 37.07 ($CH_2$), 58.52 ($CH_2$), 75.46 (CH), 167.29 (C). $^1$H-NMR (500 MHz, DMSO-$d_6$): δ 0.87 (t, J=6.9 Hz, 3H), 0.88 (t, J=6.9 Hz, 3H), 1.28-1.32 (m, 8H), 1.35 (m, 1H), 1.45 (m, 1H), 1.51 (m, 2H), 1.53 (m, 2H), 2.17 (dd, J=18.3, 8.8 Hz, 1H), 2.22 (td, J=7.2, 1.4 Hz, 2H), 2.39 (dd, J=18.3, 3.9 Hz, 1H), 2.68 (td, J=6.6, 1.6 Hz, 2H), 3.66 (td, J=6.6, 5.5 Hz, 2H), 4.00 (m, 1H), 4.57 (t br, J=5.5 Hz, OH). $^{13}$C-NMR (125 MHz, DMSO-$d_6$): δ 14.33 (2 $CH_3$), 22.35 ($CH_2$), 22.42 ($CH_2$), 24.28 ($CH_2$), 25.33 ($CH_2$), 31.22 ($CH_2$), 31.47 ($CH_2$), 31.48 ($CH_2$), 33.67 ($CH_2$), 36.62 ($CH_2$), 37.27 ($CH_2$), 57.36 ($CH_2$), 75.34 (CH), 150.37 (C), 165.59 (C).

The $^1$H-NMR (DMSO-$d_6$) showed two methylene with vicinal coupling (H-H COSY), $CH_2$ (I) ($δ_H$ 2.68, $δ_C$ 37.27), $CH_2$ (II) ($δ_H$ 3.66, 67$_C$ 57.36), Both methylene groups showed long range coupling $J_{H,C}$ (HMBC) with the acyl group carbon (Sc 165.59). Additionally, hydroxyl group ($δ_H$ 4.57) showed coupling with $CH_2$ (II) (J=5.5 Hz) and $CH_2$ (I) (J=1.6 Hz). These spectral data are in concordance with de structure of 3-hydroxipropan-2-one fragment chain. The acyl group (CO), doesn't showed coupling $J_{H,C}$ (HMBC) with other signals. Therefore, this fragment chain is linked to oxadiazine ring through N heteroatom.

Chemical shift of the CH ($δ_H$ 4.00, Sc 75.34), corresponding CH linked to oxygen heteroatom, showed a vicinal coupling (H-H) COSY with a methylene group $CH_2$ ($δ_{HA}$ 2.37 and $δ_{HB}$ 2.17) and this methylene group doesn't show coupling with other hydrogen atoms, which suggested the presence of these CH and $CH_2$ groups in oxadiazine ring. Furthermore, the CH group showed additional resonances HSQC-TOCSY with $CH_2$ ($v_C$ 33.94), $CH_2$ ($\delta_C$ 31.62), $CH_2$ ($\delta_C$ 24.36), $CH_2$ ($v_C$ 22.43 or 22.45) and $CH_3$ ($\delta_C$ 13.99), which is in concordance with n-pentyl fragment is linked to oxadiazine ring through CH-6.

On the other hand, the methylene group $CH_2$ ($\delta_H$ 2.25, $\delta_C$ 37.07), showed correlations HSQC-TOCSY with $CH_2$ ($\delta_C$ 31.34), $CH_2$ ($\delta_C$ 25.62), $CH_2$ ($\delta_C$ 22.45 or 22.43) and $CH_3$ ($\delta_C$ 13.99). The linkage between this n-pentyl chain portion and the oxadiazine ring through C-4, was determined by HMBC correlations between the imine carbon atom ($\delta_C$ 150.37) and the methylene groups $CH_2$ ($\delta_H$ 2.25) and $CH_2$ ($\delta_{HA}$ 2.37 and $\delta_{HB}$ 2.17).

Example 1—Antibiotic Activity

Bacterial Strains and Inoculum Preparation

Bacterial strains, from clinical origin, were supplied by the National Center for Microbiology, Institute of Health Carlos III (Majadahonda, Madrid). They are detailed in Table I.

TABLE I

Characteristics of strains.

| Specie | Strain | Isolation year | IMP | CTX | A/C | LIN | AMK | SxT | CIP | ERI |
|---|---|---|---|---|---|---|---|---|---|---|
| N. cyriacigeorgica | 30 | 2005 | S | S | R | S | S | S | R | R |
| N. cyriacigeorgica | 199 | 2005 | R | R | R | S | R | S | R | R |
| N. carnea | 769 | 2009 | S | S | S | S | S | R | S | R |
| N. carnea | 40 | 2011 | R | S | S | S | R | R | S | R |
| T. pulmonis | 1991 | 2009 | S | S | S | S | S | S | S | S |
| T. pulmonis | 40 | 2015 | S | R | R | R | R | R | R | R |
| M. chelonae | 870 | 2011 | R | | | R | | R | R | R |
| M. abscessus | 690 | 2012 | R | | | S | | S | R | S |
| M. fortuitum | 1080 | 2011 | R | | | R | | S | S | R |
| B. cereus | 25 | 2014 | | | | | | | | R |
| B. cereus | 182 | 2013 | | | | | | | | R |
| A. baumannii | 300 | 2001 | R | | | | R | | R | |
| A. baumannii | 1301 | 2009 | S | | | | S | | S | |
| S. aureus | 282 | 2005 | | | | | S | | R | R |
| S. aureus | 890 | 2010 | | | | | S | | S | R |
| S. epidermidis | 982 | 2006 | | | | | S | | R | R |
| S. epidermidis | 188 | 2009 | | | | | S | | S | S |

| Specie | Strain | PEN | VAN | RIF | TET | CLI | MER | CEF | TOB | GEN |
|---|---|---|---|---|---|---|---|---|---|---|
| N. cyriacigeorgica | 30 | | | | | | | | | |
| N. cyriacigeorgica | 199 | | | | | | | | | |
| N. carnea | 769 | | | | | | | | | |
| N. carnea | 40 | | | | | | | | | |
| T. pulmonis | 1991 | | | | | | | | | |
| T. pulmonis | 40 | | | | | | | | | |
| M. chelonae | 870 | R | | | | | | | | |
| M. abscessus | 690 | R | | | | | | | | |
| M. fortuitum | 1080 | R | | | | | | | | |
| B. cereus | 25 | S | S | S | R | R | | | | |
| B. cereus | 182 | S | S | S | S | R | | | | |
| A. baumannii | 300 | | | | | | R | R | S | |
| A. baumannii | 1301 | | | | | | S | R | S | |
| S. aureus | 282 | S | | S | R | | | | | R |
| S. aureus | 890 | S | | R | R | | | | | R |
| S. epidermidis | 982 | S | | S | R | | | | | R |
| S. epidermidis | 188 | S | | S | S | | | | | S |

IMP = Imipenem;
CTX = Cefotaxime;
A/C = Amoxicillin/Clavulanate;
Lin = Linezolid;
AMK = Amikacin;
SxT = Cotrimoxazole;
CIP = Ciprofloxacin;
ERI = Erythromycin;
PEN = Penicillin;
VAN = Vancomycin;
RIF = Rifampicin;
TET = Tetracycline;
CLI = Clindamycin;
MER = Meropenem;
CEF = Ceftriazone;
TOB = Tobramycin;
GEN = Gentamicin Antibacterial Susceptibility Test Bacterial cells suspension in sterile saline was prepared from a culture of 24-72 h, depending on bacterial species, in Mueller-Hinton Agar with 5% sheep blood. Each suspension was adjusted to a fixed size inoculum of $1\text{-}5\times10^8$ CFU/ml with a spectrophotometer (Ferraro, M J National Committee for Clinical Laboratory Standards. 2000).

Kirby-Bauer disk diffusion susceptibility test protocol was utilized to determine the sensitivity or resistance of pathogenic bacteria against the compounds and others antibiotics. The absence of growth around the disks is an indirect measure of the ability of this compound to inhibit an organism (Kirby, W. et al., Antibiotics Annu. 1956-1957: 892). After 18 to 72 hours of incubation at 37° C., with or without $CO_2$, under aerobic or anaerobic conditions, depending on the bacterial species, halo of growth inhibition were obtained and evaluated.

Antibiotic Activity

Interpretation of susceptibility and resistance was based on the presence or absence of a zone of inhibition surrounding the disk. Kirby-Bauer disk diffusion susceptibility test is a common method which uses antibiotic-impregnated wafers to test whether bacteria are affected by antibiotics. The size of the zone of inhibition depends on how effective the antibiotic is at stopping the growth of the bacterium. A stronger antibiotic will create a larger zone, because a lower concentration of the antibiotic is enough to stop growth.

Figure 2:
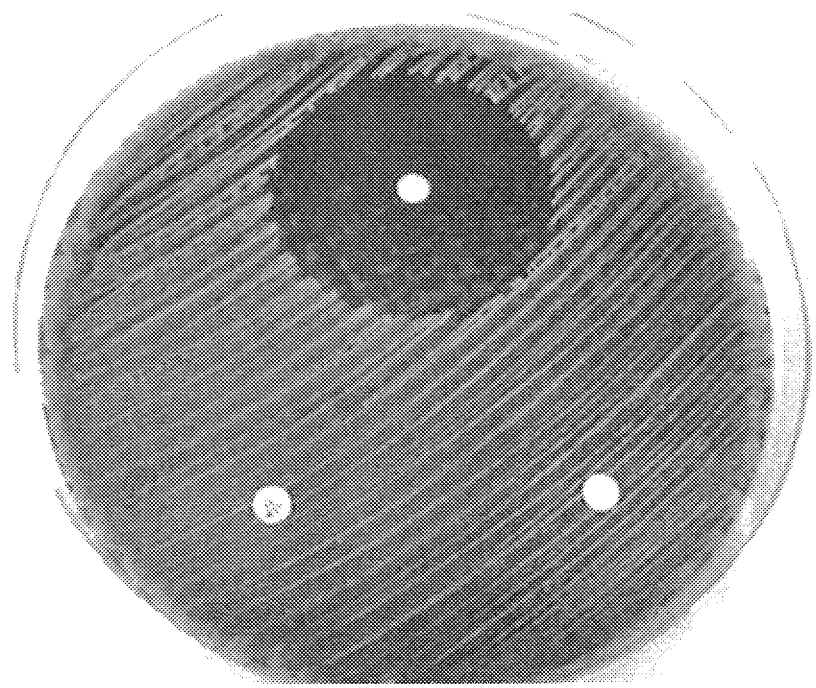
FIG. 2. Activity of the compound in *Mycobacterium abscessus*.

The results of antibiotic activity obtained with the Kirby-Bauer antibiotic test show the great potential of compounds, not only as molecules with specific activity against specific bacteria but also as possible structures for the development of broad spectrum antibiotics. The activity results are shown in Table II and some examples in FIGS. 1 and 2.

TABLE II

Antibiotic activities detected with the compound.

| Species | Activity (mm), 100 μg/disc |
|---|---|
| N. carnea | 48-50 |
| N. cyriacigeorgica | 35-38 |
| T. pulmonis | 49-52 |
| M. chelonae | 63 |
| M. abscessus | 56 |
| M. fortuitum | 44 |
| S. epidermidis | 16-18 |
| S. aureus | 20-22 |
| B. cereus | 37-40 |
| A. baumannii | 10-12 |

All compounds were tested at 100 μg/disc. The best activity was detected with *Nocardia* spp, *Tsukamurella pulmonis* and *Mycobacterium* spp. Noteworthy that the activity of compound is bactericidal in all species tested, except bacteriostatic in *B. cereus*.

Example 2—Antifungal Activity

Filamentous Fungi and Yeasts Strains and Inoculum Preparation

Filamentous fungi and yeasts strains, from clinical origin, were supplied by Microbiology Service from The Princess Hospital, Madrid. They are detailed in Table III.

TABLE III

Characteristics of the strains.

| Species | CODE | Amphotericin B | Ketoconazole | Itraconazole | Clotrimazole | Fluconazole | Voriconazole |
|---|---|---|---|---|---|---|---|
| C. parapsilosis | CP-007 | I | S | R | S | S | — |
| S. prolificans | SP-003 | R | — | — | — | — | R |
| A. fumigatus | AFu-001 | S | S | I | S | R | — |
| A. flavus | AF-001 | I | S | I | S | R | — |
| A. terreus | ATe-001 | I | S | I | S | R | — |

I = intermediate activity;
S = susceptibility;
R = Resistance

Filamentous fungi and yeast cells suspensions in distilled water was prepared from a culture of 24-48 h, depending on species, in Sabouraud agar. Each suspension was adjusted to a fixed size inoculum of $1\text{-}5\times10^8$ CFU/ml with a spectrophotometer (Ferraro, M J National Committee for Clinical Laboratory Standards. 2000).

Antifungal Susceptibility Test

Antifungal susceptibility tests were developed following the standardized methodology detailed by the European Committee on Antimicrobial Susceptibility Testing (EUCAST) documents 7.2 (method for the determination of broth dilution minimum inhibitory concentrations of antifungal agents for yeasts EDef 7.2) and 9.2 (Method for the determination of broth dilution minimum inhibitory concentrations of antifungal agents for conidia forming foulds). The compound was dissolved in DMSO and diluted with RPMI plates with 2% glucose to pH 7 with MOPS buffer. The compound was diluted in a range of concentrations from 64 to 0.12 mg/l. Plates were inoculated with a yeast suspension or filamentous fungal spores ($1\text{-}5\times10^5$ cls/ml).

Antifungal Activity

The results were evaluated after 24 hours incubation at 35° C. and absorbance reading at 530 nm. The MIC (minimum inhibitory concentration) was determined as 50% inhibition for yeasts and as 100% inhibition for filamentous fungi.

The activity results are shown in Table IV. All compounds were tested at 100 μg/disc. The best activity was exhibited in multiresistant species *Scedosporium prolificans*.

TABLE IV

Antifungal activities detected with the compound (MIC).

| Species | Fluconazole | Voriconazole | Amphotericin B | Compound |
|---|---|---|---|---|
| *Aspergillus fumigatus* | — | 0.5 | 0.5 | 0.5 |
| *Aspergillus flavus* | — | 1 | 1 | 1 |
| *Aspergillus terreus* | — | 0.5 | 2 | 0.25 |
| *Scedosporium prolificans* | — | >8 | >16 | 0.5 |
| *Candida parapsilosis* | 1 | — | — | 0.5 |

Example 3-Anti HIV Activity

Antiviral Susceptibility Test

Assessment of in vitro antiviral activity is usually performed to estimate parameters of antiviral potency and efficacy represented by the percentage of inhibition of HIV activity or IC50. The assay utilized is based on the use of recombinant viruses in which the nef gene, essential for in vitro HIV replication, has been replaced by a *Renilla* reporter gene so that viral replication can be quantified directly (Garcia-Perez J et al, J Med Virol. 2007 February; 79(2):127-37). The assay was performed infecting MT-2 cells or PHA-activated PBMCs/IL-2 with viral supernatants obtained previously. The study was development in AIDS Immunopathology Unit, Nacional Center of Microbiology, Institute of Health Carlos III, Majadahonda, Madrid, Spain.

Viability

All assays for assessing anti-HIV activity were taken in parallel to determine cellular viability of the culture in the presence or absence of different concentrations of the isolated molecule. It was followed exactly the same methodology as in the anti-HIV assay except with the addition of complete DMEM medium instead of supernatant viral, in the same proportion, and the detection of the viability was performed with the viability detection kit CellTiter Glo (Promega), following manufacturer instructions. Viability is directly proportional to the luciferase activity obtained.

All data are expressed as percentage relative to a control with DMSO at the same concentration. Antiviral activity and toxicity curves were performed to the compound at different concentrations.

Results

The profile of activity/toxicity of the compound was good with an intrinsic activity in the nanomolar range medium and a security index above 25 (Table V). The compound showed toxicity, in both MT-2 and PBMCs cells, only in the highest concentrations tested (5 and 10 µM).

TABLE V

Viability and antiviral activity.

| Concentration (µM) | Viability (%) | Viral replication (%) |
|---|---|---|
| 0 | 100 | 100 |
| 0.19 | 114 | 45 |
| 0.39 | 113 | 14 |
| 0.78 | 109 | 3 |
| 1.56 | 96 | 1 |
| 3.12 | 78 | 0 |
| 6.25 | 31 | 0 |
| 12.5 | 7 | 0 |
| 25 | 4 | 0 |
| 50 | 2 | 0 |
| 100 | 0 | 0 |

IC50 for the compound was calculated and is shown in Table VI. The IC50 was very similar in both cell lines: MT-2 (242.8 nM) and PBMCs PHA/IL-2 (362 nM). Furthermore, it could also inhibit HIV virus non-recombinant wild type (NL4.3) with a similar IC50 (333.3 nM). In conclusion, the compound was active not only in tumor lines (MT-2) but in activated peripheral blood lymphocytes (PBMCs) which supports a direct antiviral role.

TABLE VI

IC50 (half maximal inhibitory concentration) of the compound. 95% confidence interval (CI95%). CC50 means concentration of drug required to kill 50% of cells. The value R2 is a measure of goodness-of-fit of linear regression (using graphPad prism). The best value is 1.

| | $IC_{50}$ nM | CI 95% | R2 | $CC_{50}$ nM |
|---|---|---|---|---|
| Compound MT-2 | 242.8 | 102.1 to 577.4 | 0.8807 | >2500 < 5000 |
| Compound PBMCs | 362.0 | 198.4 to 660.4 | 0.9377 | >2500 < 5000 |

Activity tests were carried out on the virus entry with the compound. In this assay the infection was made, in parallel, with HIV virus (NL4.3-Ren) and HIV virus pseudotyped with the envelope of VSV (NL4.3-VSV-Luc). The compounds inhibited both viruses with the same potency, suggesting its activity is not dependent on virus entry.

Example 4—Anti-Herpes Simplex Type 1 Activity

Antiviral Susceptibility Test

In the antiviral assay a special culture plate for fluorescence assays has been used, cultivated with Vero cells (200,000 cells/ml) and infected with the recombinant herpesvirus FTKGF at 0.01 MOI (Multiplicity of infection). For the standard curve (inhibition curve pattern), increasing concentrations of a known inhibitor of HSV infection, the phosphonoacetic acid (PAA), from 0 to 200 µg/ml, were used. The compound was tested at concentrations of 45, 90, 200 and 400 nm over the virus. After 48 hours, the fluorescence intensity of FTKGF (reduction in fluorescence levels) in the plate reader Synergy HT Microplate Reader was measured.

For testing the compound action phase, Vero cells have been used, seeded at a concentration of 200,000 cells/ml. It has been used R120vGT recombinant virus at MOI 0.5 for each assay. The compound was added at concentrations of 200 and 400 nm. In addition, controls with infected untreated cells were included. The presence (antiviral action inside the cell) or absence (antiviral action on cell exterior) fluorescence was observed 72 hours post-infection.

Results

Figure 3:
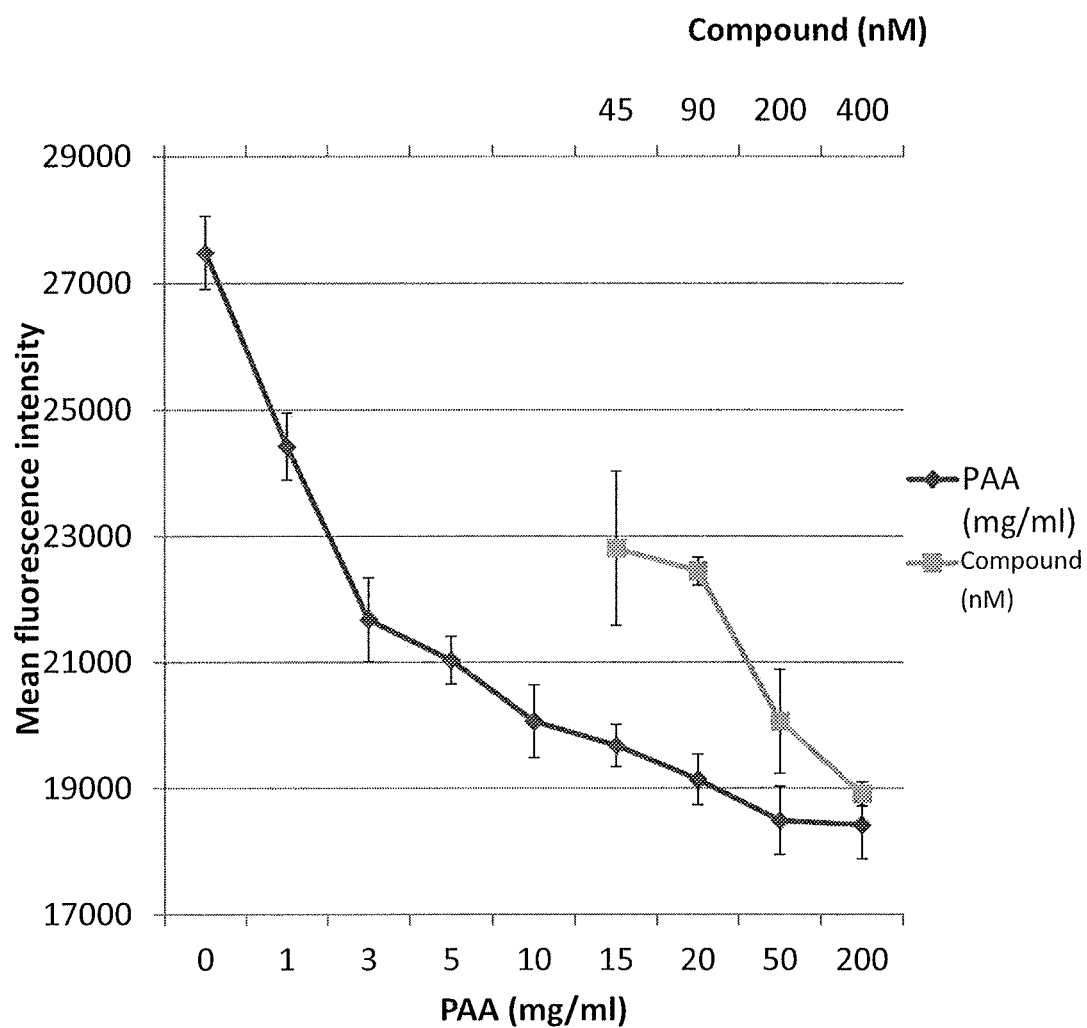
FIG. 3. Inhibitory activity of the compound in herpes simplex 1 virus.

The compound exhibited antiviral activity to 200 and, especially, 400 nM, 60% and 92% inhibition respectively (FIG. 3). It has been determined that the compound acted within the cell.

In addition, inhibition of the compound on HSV-1 and HSV-2 infections was studied by measuring the reduction of the titer of both viruses. For this, the HSV-1 and HSV-2 viruses have been analyzed in the presence and absence of compound in order to quantify and compare the viral titer reduction caused by inhibition of the molecule.

Figure 4:
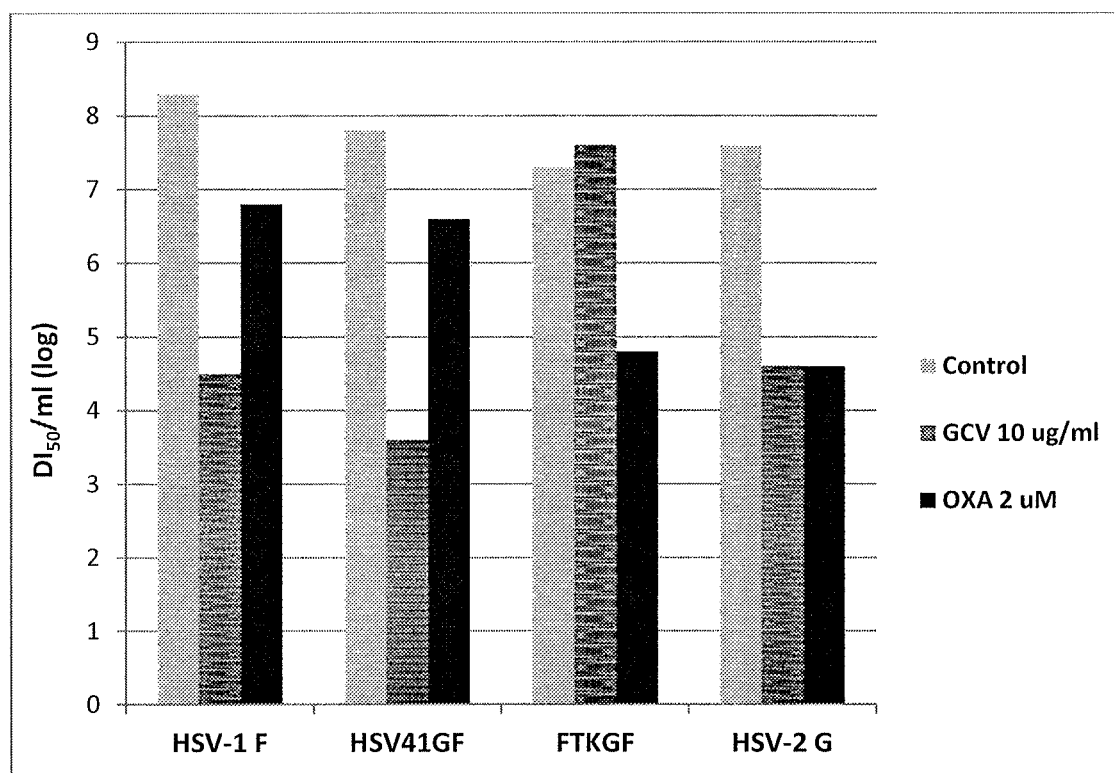
FIG. 4. Inhibitory activity of the compound in herpes virus HSV-1.

Titers of HSV-1 virus with strains F, HSV41GF (deficient in the shut-off protein), FTKGF (deficient in thymidine kinase protein) and of HSV-2 with strain G, were performed in the absence and presence of the compound at a concentration of 2 µM (FIG. 4). The antiherpetic ganciclovir (GCV) at a concentration of 10 µg/ml was included as an inhibitor control.

Results

The results show a reduction of the titer in treated virus with the compound was observed, specifically 1.5 logarithms in HSV-1, strain F, 1.2 logarithms in HSV41GF, 2.5 logarithms in FTKGF and 3 logarithms in HSV-2, strain G. The highest titer reduction produced by the compound was found in the HSV-2 strain G, where the values are similar as those obtained with the ganciclovir.

Example 5—Anti Pseudorabies Activity

Figure 5:
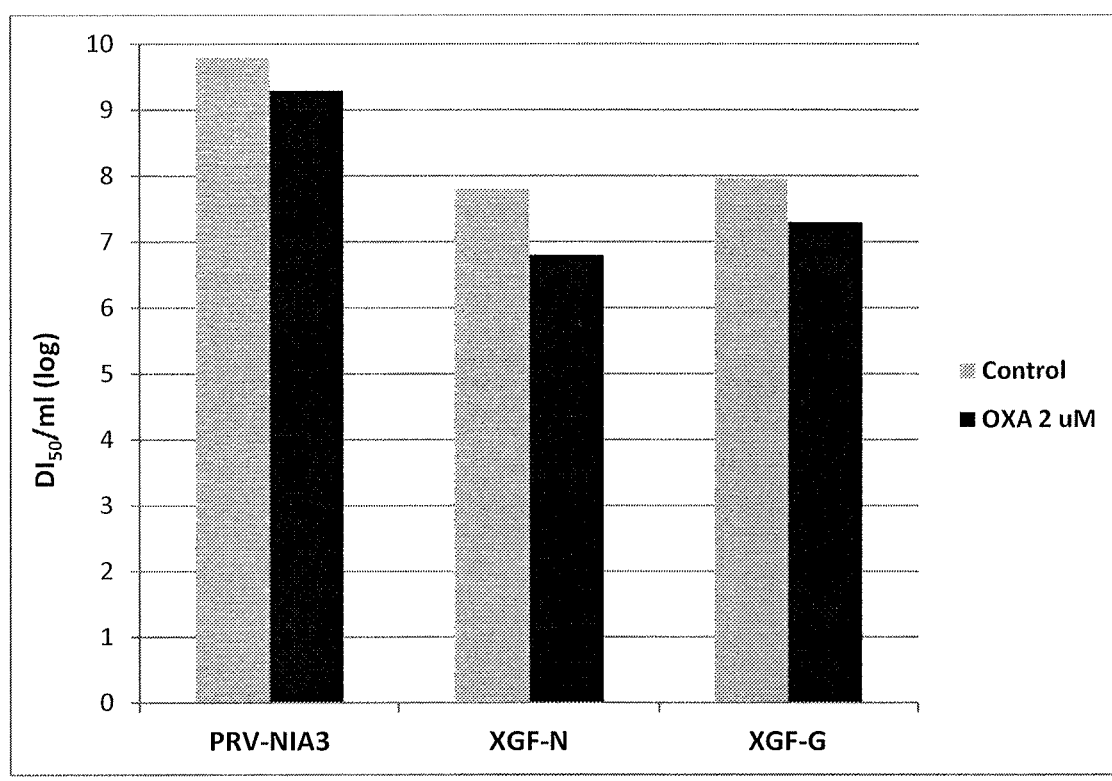
FIG. 5. Inhibitory activity of the compound in pseudorabies virus.

Titers of different porcine pseudorabies virus (PRV) have been performed in the presence and absence of the compound in order to quantify and compare the viral titer reduction caused by the inhibition of compound. Titers of PRV-NIA3, XGF-N(PRG-NIA3 deficient in the envelope glycoprotein gG) and XGF-G (gG-deficient PRV gIS8) viruses, in the absence and presence of the compound at 2 µM concentration, were performed (FIG. 5).

Results

The results show a reduction of the titer in treated viruses with the compound was observed, specifically 0.5 logarithms in PRV-NIA3, 1 logarithm in XGF-N, and 0.7 logarithms in XGF-G.

Example 6—Anti Equine Herpes Activity

Figure 6:
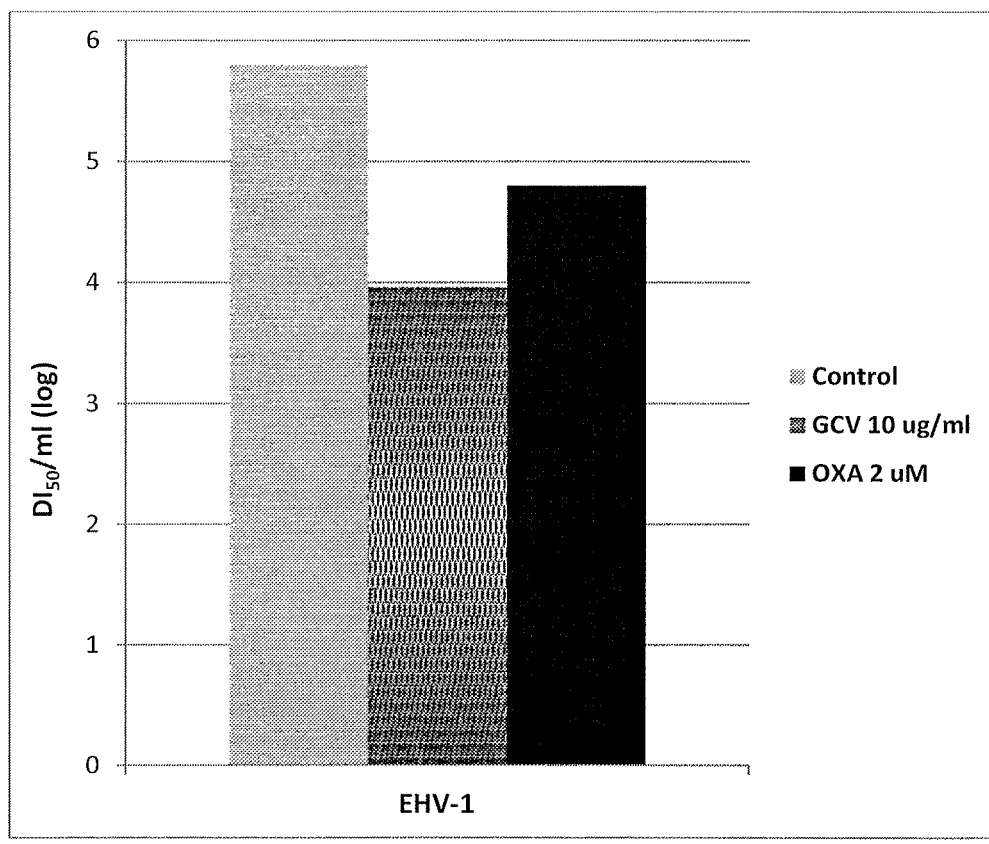
FIG. 6. Inhibitory activity of the compound in equine herpes virus.

A titer of equine herpes virus type 1 (EHV-1) was performed in the presence and absence of the compound at a concentration of 2 µM in order to quantify and compare the viral titer reduction caused by the inhibition of the compound (FIG. 6). In addition, the antiherpetic ganciclovir (GCV) at a concentration of 10 µg/ml was included as an inhibitor control.

Results

The results show a reduction of the titer in the treated virus with the compound of 1 logarithm is observed, whereas the GCV presents an inhibition of 1.8 logarithms.

Example 7—Antitumoral Activity

Material and Methods

For analysis of antitumoral activity of the compounds an MTT assay was performed with several cell lines, detailed in Table VII. With this assay it is known if there are metabolically active cells which indicate cell survival. After incubation with the compounds the reagent Bromide reagent 3-(4, 5-dimetilthiazol-2-yl)-2,5-diphenyltetrazolium was added.

TABLE VII

Characteristics of cell lines included.

| Tumor type | Cell line | Type | Mutated genes | Mutation | Alteration in the protein |
|---|---|---|---|---|---|
| Breast | MCF7 | Luminal | PIK3CA | c.1633G>A | p.E545K |
| | | | BCRA1 | c.1367T>A | p.I456T |
| | AU565 | HER2 | TP53 | c.524G>A | p.R175H |
| | | | ERBB3 | c.2854 G>C | p.E952Q |
| Head and neck | CAL33 | Squamous | TP53 | c.524G>A | p.R175H |
| | | | PIK3CA | c.3140A>G | p.H1047R |
| | | | SMAD4 | c.766C>T | p.Q256* |
| | | | APC | c.3354T>A | p.N118K |
| Colon | HT29 | Epithelial | TP53 | c.818G>A | p.R273H |
| | | | APC | c.2557 G>T | p.E853* |
| | | | PIK3CA | c.1345C>A | p.P449T |
| | | | SMAD4 | c.931C>T | p.Q311* |
| Glioblastoma | T98G | Multiforme Glioblastoma | APC | c.6985A>G | p.I2329V |
| | | | PTEN | c.1257T>G | p.L42R |
| | | | TP53 | c.711G>A | p.M237I |
| Prostate | PC3 | Adenocarcinoma | CARD11 | | |
| | | | HOXA9 | | |
| | | | WHSC1 | | |
| Lung | NCI-H1299 | CPCNP | MSH2 | c.181C>A | p.Q61K |
| | | | TP53 | c.1_954AAG | p.N596fs*3 |
| | | | NRAS | c.1786_1799>T | |
| Uterine | SK-UT-1 | leiomyosarcoma | ARID1A | c.3972delC | p.P1326fs*155 |
| | | | MSH2 | c.2363_2364delCT | p.T788fs*10 |
| | | | PIK3CA | c.263G>A | p.R88Q |
| | | | PTEN | c.950_953delTACT | p.T319fs*1 |
| | | | | c.962_963insA | p.N323fs*2 |
| Bone | HOS | Epithelial | TP53 | c.467C>G | p.R156P |
| | | | FANCF | c.148C>T | p.R50W |
| Pancreatic | CAPAN-1 | Adenocarcinoma | BRCA2 | c.5946delT | p.S1982fs*22 |
| | | | KRAS | c.35G>T | p.G12V |
| | | | TP53 | c.476> | p.I59 |

Those cells that remain active convert this reagent, through SDH (succinate dehydrogenase) enzyme, to formazan. This compound has a purple hue. The more active cells are in the medium the more formazan appears and obtain more color. With subsequent absorbance reading the inventors were able to compare cultures in different times by simple statistical analysis.

Starting from an amount of 10,000 cells per well is left about 24 hours to adhere to the plate before treatment. All tests are always in triplicate. This cell line was treated at a concentration gradient from 10 nM, 50 nM, 100 nm, 250 nm, 500 nm, and 750 nM of the compound for 24, 48 and 72 hours, using as reference negative control the same line untreated.

Results

The compound exhibited activity in all tumor cell lines tested. The product inhibited proliferation of all cell lines although variability was observed in the optimal concentration of inhibition of viability between them.

Thus, the most sensitive cell line was derived from a tumor of head and neck (CAL33) in which an inhibition at a concentration of 10 nM is obtained, being optimal from 50 nM. The second sensitive cell line was derived from a glioblastoma (T98G) which inhibited to 50 nM and showed optimal inhibition to 100 nM. In the rest of the cell lines it was observed that inhibition began to be relevant to a concentration of 100 nM and with an optimal concentration ranging between 250 and 500 nm.

In Table VIII, quantification of the best IC50 is shown (concentration of compound that inhibits 50% of cell growth) using GraphPad Prism program.

TABLE VIII

Best IC50 of the compound.

| Cell line | $IC_{50}$ to 48 hours (nM) |
|---|---|
| MCF7 | 127.33 |
| CAL33 | 42.76 |
| T98G | 106.15 |
| PC3 | 216.58 |
| NCI-H1299 | 191.50 |
| SK-UT-1 | 199.03 |
| HOS | 169.69 |

Figure 7:
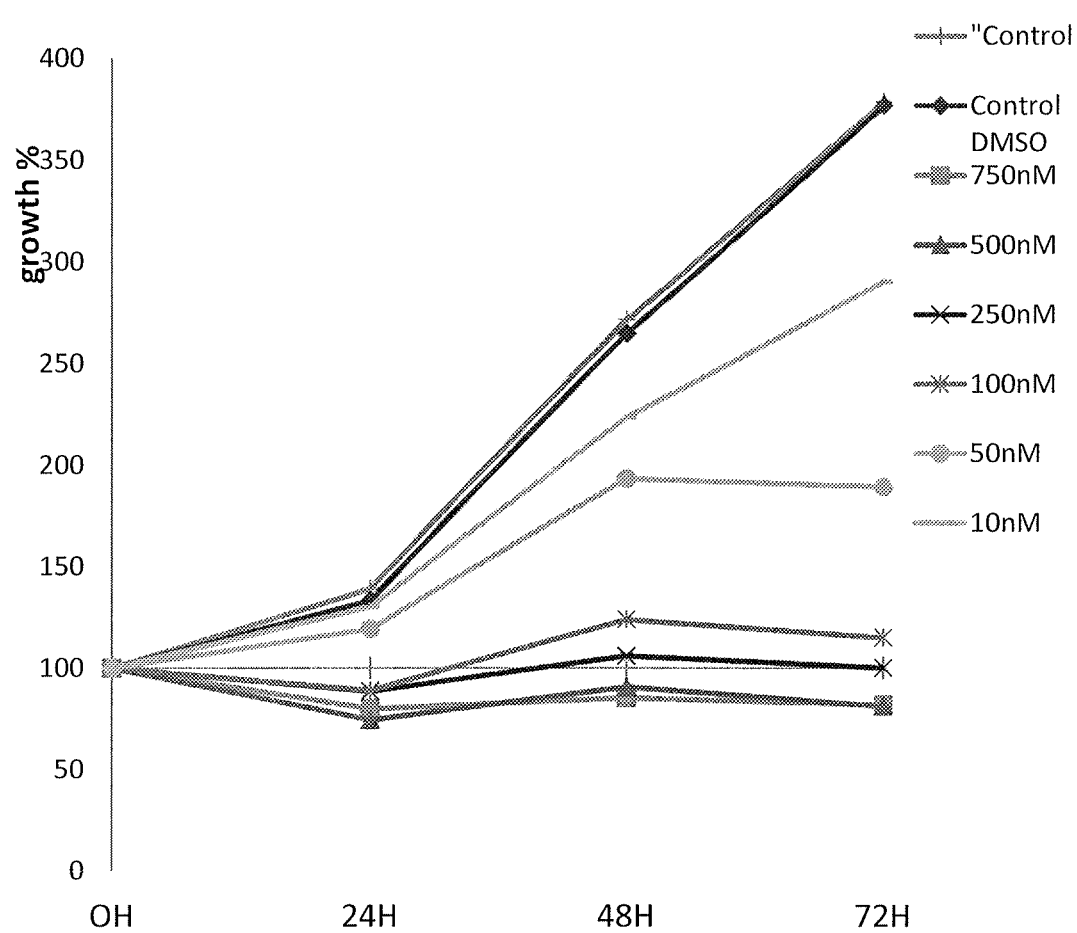
FIG. 7. Growth percentage of T98G cell line in the presence of various concentrations of the compound.
Figure 8:
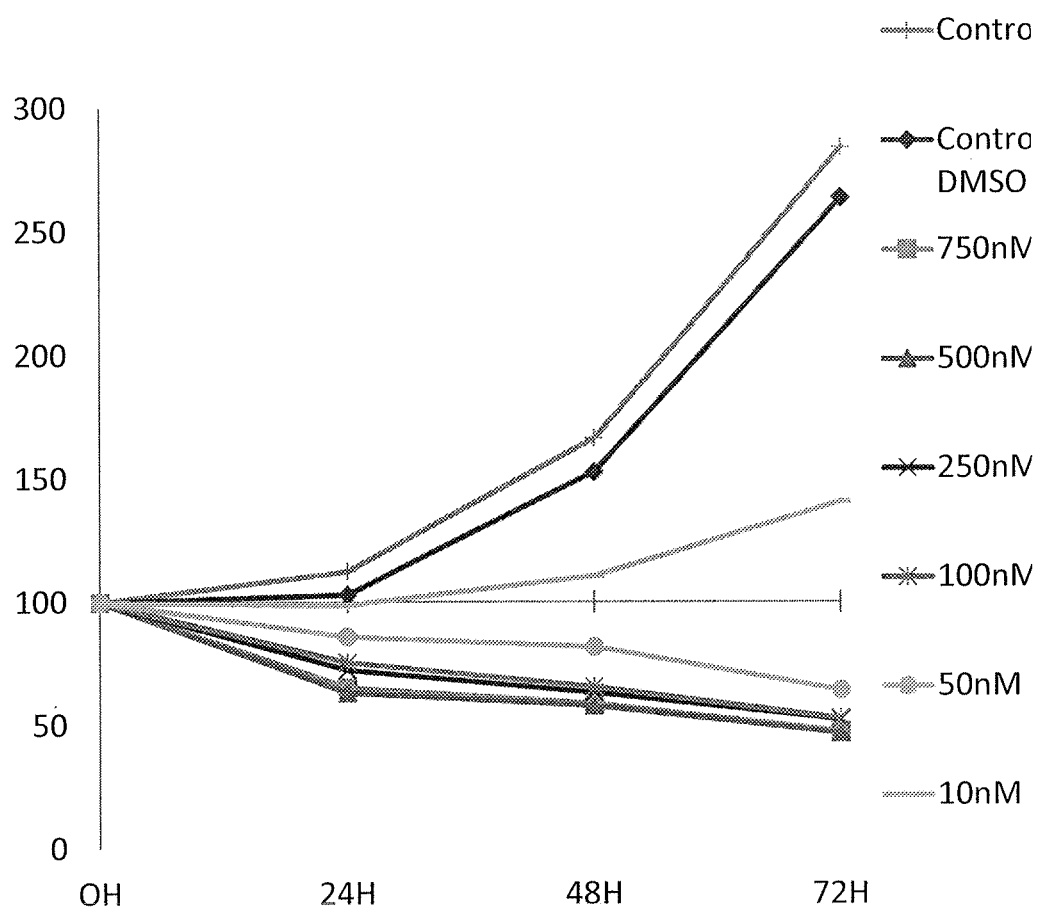
FIG. 8. Growth percentage of Ca133 cell line in the presence of various concentrations of the compound.

The FIGS. 7 and 8 show the growth percentage of the two best cell lines in the presence of various concentrations of the compound. The viability percentage was obtained by the following calculation: % viability=(DO treated cells/DO untreated cells)×100.

Untreated cells (C-) and a control incubated with solvent to the maximum concentration (C-DMSO 0.2%) were used as control of experiments.

The invention claimed is:

1. A method for treating an infection caused by a bacterium, fungus or virus and/or for treating cancer, comprising administering the compound 1-(4,6-dipentyl-5,6-dihydro-2H-1,2,3-oxadiazin-2-yl)-3-hydroxypropan-1-one, a pharmaceutically acceptable salt thereof, or solvate thereof or a pharmaceutical composition comprising said compound, or said salt, or said solvate, and a pharmaceutically acceptable excipient to a subject in need thereof, wherein the bacterium is one or more selected from the group consisting of *N. carnea, N. cyriacigeorgica, T. pulmonis, M. chelonae, M. abscessus, M. fortuitum, S. aureus, S. epidermidis, B. cereus,* and *A. baumannii,* wherein the fungi is one or more selected from the group consisting of *C. parapsilopsis, A. fumigatus, A. flavus, A. terreus,* and *S. prolificans,* wherein the virus is one or more selected from the group consisting of HIV, herpes simplex I, herpes simplex II, pseudorabies and equine herpesvirus 1, and wherein the cancer is one or more selected from the group consisting of breast, head and neck, colon, prostate, lung, glioblastoma and osteosarcoma.

2. The method of claim 1 for treating an infection caused by a bacterium, wherein the bacterium is one or more selected from the group consisting of *N. carnea, N. cyriacigeorgica, T. pulmonis, M. chelonae, M. abscessus, M. fortuitum, S. aureus, S. epidermidis, B. cereus,* and *A. baumannii.*

3. The method of claim 1 for treating an infection caused by a fungus, wherein the fungi is one or more selected from the group consisting of *C. parapsilopsis, A. fumigatus, A. flavus, A. terreus,* and *S. prolificans.*

4. The method of claim 1 for treating an infection caused by a virus, wherein the virus is one or more selected from the group consisting of HIV, herpes simplex I, herpes simplex II, pseudorabies and equine herpesvirus 1.

5. The method of claim 1 for treating cancer, wherein the cancer is one or more selected from the group consisting of breast, head and neck, colon, prostate, lung, glioblastoma and osteosarcoma.

* * * * *